United States Patent [19]

Chao et al.

[11] 4,243,586
[45] Jan. 6, 1981

[54] STEROIDAL-17-SPIRO-DIHYDROFURA-NONES

[75] Inventors: Sam T. Chao, East Windsor; Ravi K. Varma, Belle Mead, both of N.J.

[73] Assignee: E. R. Squibb & Sons, Inc., Princeton, N.J.

[21] Appl. No.: 113,153

[22] Filed: Jan. 18, 1980

[51] Int. Cl.³ .............................................. C07J 71/00
[52] U.S. Cl. .................................... 260/239.55 R
[58] Field of Search ................................. 260/239.55

[56] References Cited

U.S. PATENT DOCUMENTS

| | | | |
|---|---|---|---|
| 3,642,780 | 2/1972 | Alvarez | 260/239.55 R |
| 3,644,340 | 2/1972 | Berkoz | 260/239.55 D |
| 3,757,009 | 9/1973 | Anner | 260/239.55 R |
| 3,945,997 | 3/1976 | Cimarusti | 424/241 |

*Primary Examiner*—Elbert L. Roberts

*Attorney, Agent, or Firm*—Lawrence S. Levinson; Donald J. Barrack

[57] ABSTRACT

Steroidal-17-spiro-dihydrofuranones, i.e., steroid having in the 17-position a group having the partial structural formula

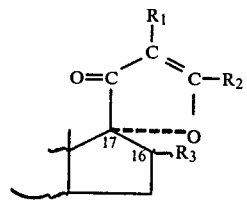

wherein $R_1$ is bromine, chlorine, or fluorine; $R_2$ is alkyl, aryl, or arylalkyl; $R_3$ is hydrogen, α-methyl, β-methyl, hydroxy or a conventional hydrolyzable ester thereof, have topical antiinflammatory activity.

11 Claims, No Drawings

STEROIDAL-17-SPIRO-DIHYDROFURANONES

BACKGROUND OF THE INVENTION

17-Halo-17-acyloxypregnenes are known in the art to have topical antiinflammatory activity. Representative of the art disclosing these steroids are U.S. Pat. Nos. 3,642,780 and 3,644,340.

U.S. Pat. No. 3,757,009 discloses steroids having the following partial structure

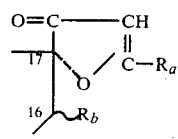

wherein $R_a$ is hydrogen, alkyl, aryl or arylalkyl and $R_b$ is hydrogen, methyl, hydroxyl, esterified hydroxyl or $\beta$-halogen. The steroids are said to be useful as, inter alia, antiinflammatory agents.

BRIEF DESCRIPTION OF THE INVENTION

Steroids having the formula

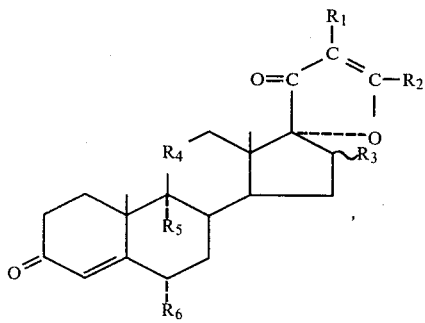

and the 1,2-dehydro derivatives thereof, have topical antiinflammatory activity. In formula I, and throughout the specification, the symbols are as defined below.

$R_1$ is bromine, chlorine or fluorine;
$R_2$ is alkyl, aryl, or arylalkyl;
$R_3$ is hydrogen, $\alpha$-methyl, $\beta$-methyl, hydroxy or a conventional hydrolyzable ester thereof;
$R_4$ is carbonyl or $\beta$-hydroxymethylene;
$R_5$ is bromine, chlorine or fluorine; and
$R_6$ is hydrogen, bromine, fluorine or methyl.

The terms "alkyl" and "alkoxy" as used throughout the specification, refer to groups having 1 to 8 carbon atoms.

The term "aryl", as used throughout the specification, refers to phenyl or phenyl substituted with one or two alkyl, alkoxy, or halogen (chlorine, fluorine, bromine or iodine) groups.

The term "conventional hydrolyzable ester", as used throughout the specification, refers to those hydrolyzable carboxylic acid ester groups conventionally employed in the steroid art, particularly those derived from carboxylic acids having the formula

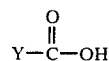

wherein Y is alkyl or aryl.

DETAILED DESCRIPTION OF THE INVENTION

The steroids of this invention can be prepared from the corresponding 21-halopregnenes having the formula

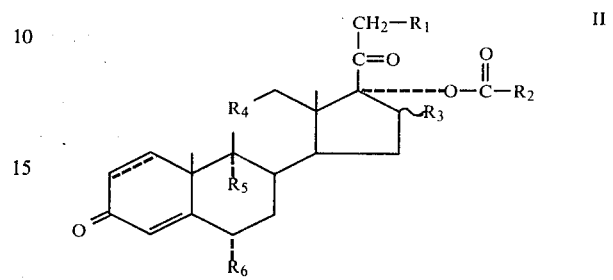

In formula II, and throughout the specification, a dotted line in the 1,2-position represents the optional presence of ethylenic unsaturation. The starting steroids of formula II are known in the art; see, for example, U.S. Pat. No. 3,642,780, issued Feb. 15, 1972; U.S. Pat. No. 3,644,340, issued Feb. 22, 1972; and U.S. Pat. No. 3,832,366, issued Aug. 27, 1974.

Treatment of a steroid of formula II with a non-nucleophilic organic base yields the products of this invention. The reaction can be run in an organic solvent, e.g., an aliphatic hydrocarbon such as toluene, preferably under reflux conditions. Exemplary of the non-nucleophilic organic bases which can be used to prepare the steroids of this invention are 1,5-diazabicyclo[5,4,0]undec-5-ene (referred to in the art as DBU), 1,4-diazabicyclo[2,2,2]-octane (referred to in the art as DABCO) and 1,5-diazabicyclo[4,3,0]non-5-ene (referred to in the art as DBN).

Preferred steroids of this invention are those having the formula

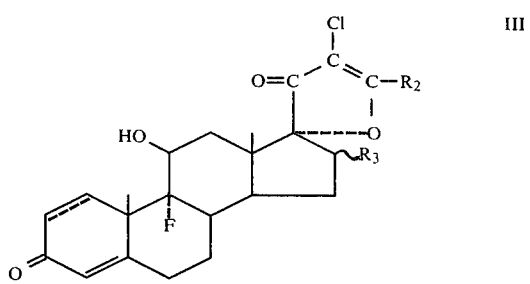

The steroids of this invention are physiologically active substances that possess glucocorticoid and antiinflammatory activity. They can be used topically in lieu of known glucocorticoids in the treatment of skin conditions such as dermatitis, sunburn, neurodermatitis, eczema, and anogenital pruritus. The compounds of this invention may be used in the range of 0.01 to 5.0% by weight, preferably 0.05 to 2.0% by weight, in a conventional cream or lotion.

The following examples are specific embodiments of this invention.

EXAMPLE 1

(11β,17R)-4'-Chloro-9-fluoro-11-hydroxy-5'-phenyl-spiro[androst-4-ene-17,2'(3'H)-furan]-3,3'-dione A solution of 533 mg (1.06 mmole) of 21-chloro-9-fluoro-11β,17-dihydroxypregn-4-ene-3,20-dione, 17-benzoate in 120 ml of dry toluene is refluxed with 483 mg (3.18 mmole) of 1,5-diazabicyclo[5,4,0]undec-5-ene in a soxhlet extraction apparatus packed with molecular sieves 4A to remove the water produced in the reaction. After 22 hours the solution is cooled and the solvent is removed in vacuo. The residue is dissolved in chloroform, and the chloroform solution is washed with 5% hydrochloric acid solution and water, dried over anhydrous $Na_2SO_4$ and evaporated in vacuo. The residue is dissolved in chloroform-hexane (7:3) and chromatographed on a 60 g-silica gel column. Elution with chloroform-hexane (7:3) gives 410 mg of material. One crystallization from chloroform-methanol-hexane gives 280 mg of the title compound, melting point 316°–318° C., with consistant spectral data.

Anal. Calc'd for $C_{28}H_{30}ClFO_4$:C, 69.34; H, 6.24; Cl, 7.31; F, 3.92: Found: C, 69.59; H, 6.02; Cl, 7.60; F, 3.81.

EXAMPLE 2

(11β,17R)-4'-Chloro-5'-ethyl-9-fluoro-11-hydroxyspiro[androst-4-eno-17,2'(3'H)-furan]-3,3'-dione A solution of 1.4 g (3.08 mmole) of 21-chloro-9-fluoro-11β,17-dihydroxypregn-4-ene-3,20-dione, 17-propionate in 180 ml of dry toluene is refluxed with 0.3 ml of 1,5-diazabicyclo[5,4,0]unded-5-ene in an apparatus equipped to remove the water produced in the reaction. After 20 hours the solution is cooled and the solvent is removed in vacuo. The residue is dissolved in chloroform, and the chloroform solution is washed with 5% hydrochloric acid solution and water, dried over anhydrous $Na_2SO_4$ and evaporated in vacuo. The residue is dissolved in 3:7 hexane-chloroform and chromatographed on a 110 g-silica gel column. Elution with hexane-chloroform (3:7, 1:4 and 1:9) gives 0.99 g of material. One crystallization from acetone-hexane gives 0.78 g of the title compound, melting point 278°–280° C., with consistent spectral data.

Anal. Calc'd for $C_{24}H_{30}ClFO_4$: C, 65.97; H, 6.92; Cl, 8.12; F, 4.35; Found: C, 65.94; H, 6.72; Cl, 8.10; F, 4.30.

EXAMPLES 3–11

Following the procedure of Example 1, but substituting the steroid listed in column I for 21-chloro-9-fluoro-11β,17-dihydroxypregn-4-ene-3,20-dione, 17-benzoate, yields the steroid listed in column II.

|    | Column I | Column II |
|----|----------|-----------|
| 3. | 21-chloro-9-fluoro-11β,17-dihydroxy-pregna-1,4-diene-3,20-dione,17-acetate | (11β,17R)-4'-chloro-9-fluoro-11-hydroxy-5'-methylspiro[androsta-1,4-dieno-17,2'(3'H)-furan]-3,3'-dione |
| 4. | 9,21-difluoro-11β,17-dihydroxypregna-1,4-diene-3,20-dione,17-phenylacetate | (11β,17R)-4',9-difluoro-11-hydroxy-5'-(phenylmethyl)spiro[androsta-1,4-dieno-17,2' (3'H)-furan]-3,3'-dione |
| 5. | 21-bromo-6,9-difluoro-17-hydroxypregn-4-ene-3,11,20-trione,17-benzoate | (17R)-4'-bromo-6,9-difluoro-5'-phenylspiro[androst-4-ene-17,2'-(3'H)-furan]-3,3',11-trione |
| 6. | 6α,9,21-tribromo-11β,17-dihydroxypregna-1,4-diene-3,20-dione,16-propionate | (6α,11β,17R)-4',6,9-tribromo-5'-ethyl-11-hydroxyspiro[androsta-1,4-dieno-17,2' (3'H)-furan]-3,3'-dione |
| 7. | 9,21-dichloro-11β,17-dihydroxy-6α-methylpregna-1,4-diene-3,20-dione,-17-benzoate | (6α,11β,17R)-4',9-dichloro-11-hydroxy-6-methyl-5'-phenylspiro[androsta-1,4-dieno-17,2'(3'H)-furan]-3,3'-dione |
| 8. | 21-chloro-9-fluoro-11β,17-dihydroxy-16α-methylpregn-4-ene-3,20-dione,17-propionate | (11β,16α,17R)-4'-chloro-5'-ethyl-9-fluoro-11-hydroxy-16-methylspiro-3,3'-dione |
| 9. | 21-chloro-9-fluoro-11β,17-dihydroxy-16β-methylpregn-4-ene-3,20-dione,17-propionate | (11β,16β,17R)-4'-chloro-5'-ethyl-9-fluoro-11-hydroxy-16-methylspiro[androst-4-ene-17,2'(3'H)-furan]3,3'-dione |
| 10. | 21-chloro-9-fluoro-11β,16α,17-tri-hydroxypregn-4-ene-3,20-dione,17-propionate | (11β,16α,17R)-4'-chloro-5'-ethyl-9-fluoro-11,16-dihydroxy[androst-4-ene-17,2'(3'H)-furan]-3,3'-dione |
| 11. | 21-chloro-9-fluoro-11β,16α,17-tri-hydroxypregn-4-ene-3,20-dione,16,17-dipropionate | (11β,16α,17R)-4'-chloro-5'-ethyl-9-fluoro-11,16-dihydroxy[androst-4-ene-17,2'(3'H)-furan]-3,3'-dione,-16-propionate |

What is claimed is:

1. A steroid having the formula

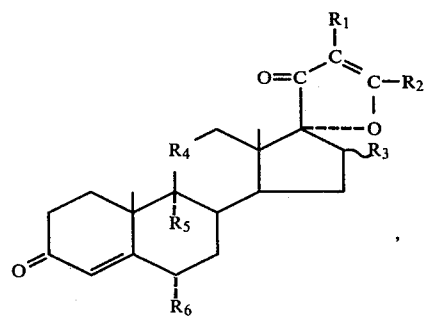

or the 1,2-dehydro derivative thereof, wherein $R_1$ is bromine, chlorine, or fluorine; $R_2$ is alkyl, aryl, or arylalkyl; $R_3$ is hydrogen, α-methyl, β-methyl, hydroxy or a conventional hydrolyzable ester thereof; $R_4$ is carbonyl or β-hydroxymethylene; $R_5$ is bromine, chlorine or fluorine; and $R_6$ is hydrogen, bromine, fluorine or methyl.

2. A steroid in accordance with claim 1 wherein $R_2$ is alkyl.

3. A steroid in accordance with claim 1 wherein $R_2$ is aryl.

4. A steroid in accordance with claim 1 wherein $R_2$ is arylalkyl.

5. A steroid in accordance with claim 1 wherein $R_1$ is chloro.

6. A steroid in accordance with claim 1 wherein $R_3$ is hydrogen.

7. A steroid in accordance with claim 1 wherein $R_4$ is β-hydroxymethylene.

8. A steroid in accordance with claim 1 wherein $R_5$ is fluorine.

9. A steroid in accordance with claim 1 having the formula

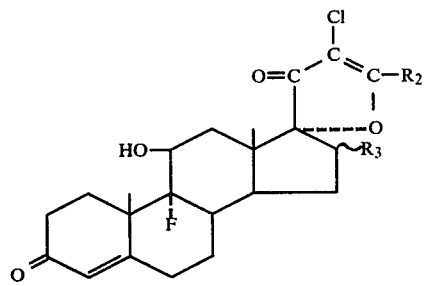

or the 1,2-dehydro derivative thereof.

10. The steroid in accordance with claim 1, (11β,17R)-4'-chloro-9-fluoro-11-hydroxy-5'-phenyl-spiro[androst-4-ene-17,2'(3'H)-furan]-3,3'-dione.

11. The steroid in accordance with claim 1, (11β,17R)-4'-chloro-5'-ethyl-9-fluoro-11-hydroxyspiro[androst-4-eno-17,2'(3'H)-furan]-3,3'-dione.

* * * * *

UNITED STATES PATENT AND TRADEMARK OFFICE
CERTIFICATE OF CORRECTION

PATENT NO. : 4,243,586
DATED : January 6, 1981
INVENTOR(S) : Sam T. Chao, et al.

It is certified that error appears in the above—identified patent and that said Letters Patent are hereby corrected as shown below:

In the table bridging columns 3 and 4, the compound named in column II of example 8 should read: --(11$\beta$,16$\alpha$,17R)-4'-chloro-5'-ethyl-9-fluoro-11-hydroxy-16-methylspiro[androst-4-ene-17,2'(3'H)-furan]-3,3'-dione--

Column 3, line 49, "consistant" should read --consistent--

Signed and Sealed this

Twenty-fifth Day of August 1981

[SEAL]

Attest:

GERALD J. MOSSINGHOFF

Attesting Officer

Commissioner of Patents and Trademarks